US012011609B2

(12) United States Patent
Schneider et al.

(10) Patent No.: US 12,011,609 B2
(45) Date of Patent: Jun. 18, 2024

(54) WEARABLE CARDIOVERTER DEFIBRILLATOR (WCD) SYSTEM USING SECURITY NFC TAG FOR REQUESTS OF DATA FROM MEMORY

(71) Applicant: West Affum Holdings DAC, Dublin (IE)

(72) Inventors: Erik L. Schneider, Issaquah, WA (US); Erick Michael Roane, Kirkland, WA (US); Dusan Beblavy, Kosice (SK)

(73) Assignee: West Affum Holdings DAC, Dublin (IE)

( * ) Notice: Subject to any disclaimer, the term of this patent is extended or adjusted under 35 U.S.C. 154(b) by 324 days.

(21) Appl. No.: 17/156,141

(22) Filed: Jan. 22, 2021

(65) Prior Publication Data

US 2021/0138255 A1    May 13, 2021

Related U.S. Application Data

(60) Continuation of application No. 16/211,086, filed on Dec. 5, 2018, now Pat. No. 10,946,208, which is a
(Continued)

(51) Int. Cl.
*A61N 1/39* (2006.01)
*A61N 1/04* (2006.01)
(Continued)

(52) U.S. Cl.
CPC ........... *A61N 1/3993* (2013.01); *A61N 1/046* (2013.01); *A61N 1/3968* (2013.01);
(Continued)

(58) Field of Classification Search
CPC ...... A61N 1/39; A61N 1/3904; A61N 1/3944; A61N 1/3968; A61N 1/3993; A61N 1/37252; A61N 1/37254; A61N 1/37264
See application file for complete search history.

(56) References Cited

U.S. PATENT DOCUMENTS 3,724,455 A    4/1973 Unger
4,583,524 A    4/1986 Hutchins
(Continued)

FOREIGN PATENT DOCUMENTS

CN    1554166 A    12/2004
CN    205549235 U    9/2016
(Continued)

OTHER PUBLICATIONS

Extended European Search Report for EP Application No. 17174698.5-1124 dated Feb. 9, 2018.
(Continued)

*Primary Examiner* — George R Evanisko
(74) *Attorney, Agent, or Firm* — Spectrum IP Law Group LLC

(57) ABSTRACT

A wearable cardioverter defibrillator (WCD) system includes a processor, a memory, a wireless communication module (DWCM), and an NFC tag that stores information for how an accessing device may access the DWCM wirelessly. An accessing device such as a defibrillator configurator with an NFC reader may read the NFC tag of the WCD system, if it has adequate permission to do so. Upon so reading, the accessing device will know how to address the DWCM wirelessly, and thus install or update configuration data, software updates, or request memory downloads from operations. The use of the NFC tag requires close proximity, which hampers both inadvertently programming the wrong WCD system, plus a WCD system being attacked maliciously.

9 Claims, 13 Drawing Sheets

Related U.S. Application Data division of application No. 15/364,401, filed on Nov. 30, 2016, now Pat. No. 10,179,246.

(60) Provisional application No. 62/263,550, filed on Dec. 4, 2015.

(51) Int. Cl.

| | |
|---|---|
| *G06F 21/44* | (2013.01) |
| *G06F 21/62* | (2013.01) |
| *G16H 20/30* | (2018.01) |
| *G16H 20/40* | (2018.01) |
| *G16H 40/63* | (2018.01) |
| *G16Z 99/00* | (2019.01) |
| *H04L 9/40* | (2022.01) |
| *H04W 4/00* | (2018.01) |
| *H04W 12/30* | (2021.01) |

(52) U.S. Cl.
CPC .......... *A61N 1/3987* (2013.01); *G06F 21/44* (2013.01); *G06F 21/6245* (2013.01); *G16H 20/30* (2018.01); *G16H 20/40* (2018.01); *G16H 40/63* (2018.01); *G16Z 99/00* (2019.02); *H04L 63/0428* (2013.01); *H04W 4/00* (2013.01); *H04W 12/35* (2021.01); *H04L 63/0492* (2013.01)

(56) References Cited

U.S. PATENT DOCUMENTS

| | | |
|---|---|---|
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,474,574 A | 12/1995 | Payne et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,805,190 B2 | 9/2010 | Chapman et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 2011/0022105 A9 | 1/2003 | Owen et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0155336 A1 | 7/2006 | Heath |
| 2008/0312709 A1 | 12/2008 | Volpe et al. |
| 2009/0005827 A1 | 1/2009 | Weintraub et al. |
| 2010/0007413 A1 | 1/2010 | Herleikson et al. |
| 2010/0298899 A1 | 11/2010 | Donnelly et al. |
| 2011/0288604 A1 | 11/2011 | Kaib et al. |
| 2011/0288605 A1 | 11/2011 | Kaib et al. |
| 2012/0150008 A1 | 1/2012 | Lanar et al. |
| 2012/0112903 A1 | 5/2012 | Kaib et al. |
| 2012/0144551 A1 | 6/2012 | Guldalian |
| 2012/0158075 A1 | 6/2012 | Kaib et al. |
| 2012/0191147 A1* | 7/2012 | Rao .................. G16H 20/30 |
| | | 607/3 |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0304143 A1 | 11/2013 | Banville |
| 2013/0317852 A1 | 11/2013 | Worrell et al. |
| 2013/0325078 A1 | 12/2013 | Whiting et al. |
| 2014/0005736 A1 | 1/2014 | Geheb |
| 2014/0025131 A1 | 1/2014 | Sullivan et al. |
| 2014/0051962 A1* | 2/2014 | Krusor ................ A61B 5/0531 |
| | | 600/386 |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2015/0331996 A1 | 11/2015 | Gustavson et al. |
| 2016/0004831 A1 | 1/2016 | Carlson et al. |
| 2016/0082277 A1 | 3/2016 | Foshee, Jr. et al. |
| 2016/0283900 A1 | 9/2016 | Johnson et al. |
| 2017/0128735 A1 | 5/2017 | Gustavson et al. |

FOREIGN PATENT DOCUMENTS

| | | |
|---|---|---|
| WO | 9839061 A2 | 9/1998 |
| WO | 0206992 A2 | 1/2002 |
| WO | 2014134225 A2 | 9/2014 |
| WO | 2014201336 A1 | 12/2014 |
| WO | 2015017718 A1 | 2/2015 |

OTHER PUBLICATIONS

Heartstart MRx and XL AED Algorithm—Application Note, Jul. 2001, Edition 2 Philips Healthcare, USA.

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(56) References Cited

OTHER PUBLICATIONS

Lifecor LifeVest System Model WCD 3100 Operator's Manual, 2006, PN 20B0040 Rev FI, Zoll Lifecor Corporation, Pittsburgh, PA.
LifeVest Model 4000 Patient Manual, Zoll, 2009, PN 20B0047 Rev B.
Pagan-Carlo, et al., "Encircling Overlapping Multipulse Shock Waveforms for Transthoracic Defibrillation," JACC Journals, Dec. 1998, vol. 32 Issue 7, p. 2065-2071.
The LifeVest Network/Patient Data Management System, Zoll, 2015, 2000503 Rev A.
Cui H, Yao S. [Key Technology and Quantity Control of Wearable Medical Devices]. Zhongguo Yi Liao Qi Xie Za Zhi. Mar. 2015;39(2):113-7, 121. Chinese. PMID: 26204741.
First Office action dated Jan. 10, 2022 in CN Patent Application No. 201710409214.8.

\* cited by examiner

FIG. 1  *SAMPLE COMPONENTS OF WEARABLE CARDIOVERTER DEFIBRILLATOR (WCD) SYSTEM*

SAMPLE COMPONENTS OF EXTERNAL DEFIBRILLATOR

FIG. 5 — METHODS

FIG. 7     *METHODS*

FIG. 9 — METHODS

WEARABLE CARDIOVERTER DEFIBRILLATOR (WCD) SYSTEM USING SECURITY NFC TAG FOR REQUESTS OF DATA FROM MEMORY

CROSS REFERENCE TO RELATED PATENT APPLICATIONS

The present application is a continuation of U.S. application Ser. No. 16/211,086 filed Dec. 5, 2018 (pending), which in turn is a divisional of U.S. application Ser. No. 15/364,401 filed Nov. 30, 2016, now U.S. Pat. No. 10,179,246. Said application Ser. No. 15/364,401 claims the benefit of U.S. Appl. No. 62/263,550 filed on Dec. 4, 2015. Said application Ser. No. 16/211,096, said application Ser. No. 15/364,401, and said Application No. 62/263,550 are hereby incorporated herein by reference in their entireties.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g., within 10 minutes, unless treated in the interim.

Some people have an increased risk of SCA. People at a higher risk include patients who have had a heart attack, or a prior SCA episode. A frequent recommendation is for these people to receive an implantable cardioverter defibrillator (ICD). The ICD is surgically implanted in the chest, and continuously monitors the patient's electrocardiogram (ECG). If certain types of heart arrhythmias are detected, then the ICD delivers an electric shock through the heart.

After being identified as having an increased risk of an SCA, and before receiving an ICD, these people are sometimes given a wearable cardioverter defibrillator (WCD) system. (Early versions of such systems were called wearable cardiac defibrillator systems.) A WCD system typically includes a harness, vest, or other garment that the patient is to wear. The WCD system includes a defibrillator and electrodes, coupled to the harness, vest, or other garment. When the patient wears the WCD system, the external electrodes may then make good electrical contact with the patient's skin, and therefore can help determine the patient's ECG. If a shockable heart arrhythmia is detected, then the defibrillator delivers the appropriate electric shock through the patient's body, and thus through the heart.

WCD systems may communicate electronically with other devices. A challenge, however, may arise from communications that are inadvertent or, worse, malicious, for example when a WCD system is to be programmed.

BRIEF SUMMARY

The present description gives instances of wearable cardioverter defibrillator (WCD) systems, storage media that store programs, and methods, the use of which may help overcome problems and limitations of the prior art.

In embodiments, a wearable cardioverter defibrillator (WCD) system includes a processor, a memory, a wireless communication module (DWCM), and an NFC tag that stores information for how an accessing device may access the DWCM wirelessly. An accessing device such as a defibrillator configurator with an NFC reader may read the NFC tag of the WCD system, if it has adequate permission to do so. Upon so reading, the accessing device will know how to address the DWCM wirelessly, and thus install or update configuration data, software updates, or request memory downloads from operations. The use of the NFC tag requires close proximity, which hampers both inadvertently programming the wrong WCD system, plus a WCD system being attacked maliciously.

Other advantages include that no manual entry of the connectivity data is required, and no physical cable is required in all embodiments. A physical cable is for a wired that requires the defibrillator configurator to be physically connected. This limits the configuring workflow because of physical limitations plus presents tripping hazards. Moreover, manual entry of the connectivity data also presents disadvantages because of security and ease of use. Manual entry of addresses and passwords presents a security risk because address and passwords would need to be in a human readable format which could be inappropriately shared with other people. Also the workflow of manually entering in data is cumbersome and error prone.

These and other features and advantages of the claimed invention will become more readily apparent in view of the embodiments described and illustrated in the present disclosure, namely from the present written specification and the drawings. In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

DETAILED DESCRIPTION

As has been mentioned, the present description is about wearable cardioverter defibrillator (WCD) systems, storage media that store programs, and methods. Embodiments are now described in more detail.

A wearable cardioverter defibrillator (WCD) system made according to embodiments has a number of components. These components can be provided separately as modules that can be interconnected, or can be combined with other components, etc.

A component of a WCD system can be a support structure, which is configured to be worn by the patient. The support structure can be any structure suitable for wearing, such as a harness, a vest, a half-vest—for example over the left side of the torso that positions electrodes on opposite sides of the heart, one or more belts that are configured to be worn horizontally or possibly vertically over a shoulder, another garment, and so on. The support structure can be implemented in a single component or multiple components. For example, a support structure may have a top component resting on the shoulders, for ensuring that the defibrillation electrodes will be in the appropriate positions for defibrillating, and a bottom component resting on the hips, for carrying the bulk of the weight of the defibrillator. A single component embodiment could be with a belt around at least the torso. Other embodiments could use an adhesive material or another way for attaching to the patient, without encircling any part of the body. There can be other examples.

Figure 1:
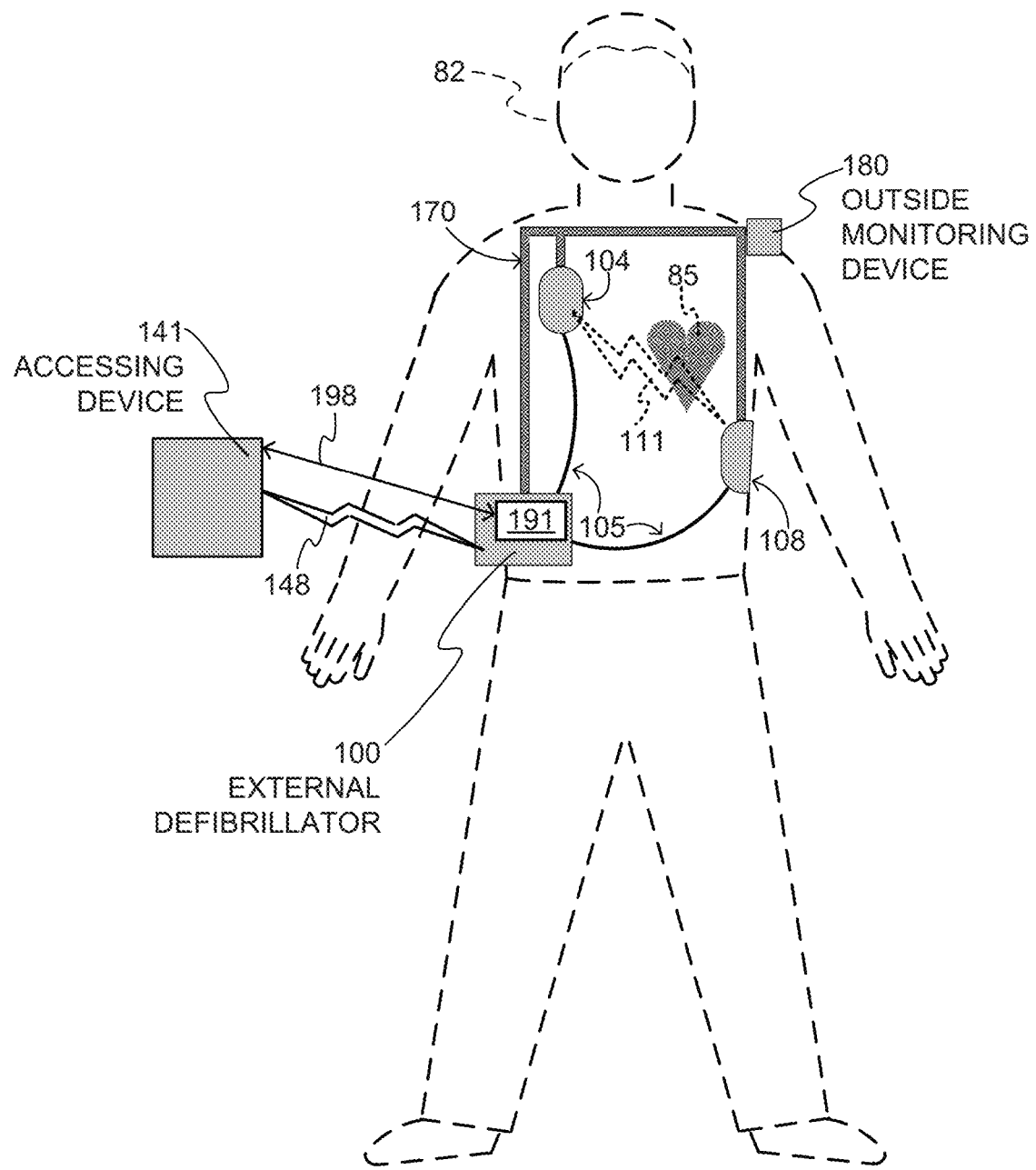
FIG. 1 is a diagram of components of a sample wearable cardioverter defibrillator (WCD) system, made according to embodiments.

FIG. 1 depicts components of a WCD system made according to embodiments, as it might be worn by a patient 82. A patient such as patient 82 may also be referred to as a person and/or wearer, since that patient wears components of the WCD system.

In FIG. 1, a generic support structure 170 is shown relative to the body of patient 82, and thus also relative to his or her heart 85. Structure 170 could be a harness, a vest, a half-vest, one or more belts, or a garment, etc., as per the above. Structure 170 could be implemented in a single component, or multiple components, and so on. Structure 170 is wearable by patient 82, but the manner of wearing it is not depicted, as structure 170 is depicted only generically in FIG. 1 and, in fact, partly conceptually. That is, FIG. 1 is provided merely to illustrate concepts about the support structure 170 and is not to be construed as limiting it.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 are coupled to support structure 170. As such, many of the components of defibrillator 100 can be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111, also known as a defibrillation shock or therapy shock, is intended to go through and restart heart 85, in an effort to save the life of patient 82. Pulse 111 can further include one or more pacing pulses, and so on.

A WCD system according to embodiments includes a Near Field Communications (NFC) tag. The NFC tag typically includes a tag antenna, a tag processor, and a tag memory, and operates according to principles of RFID (Radio Frequency Identification). The NFC tag may be provided anywhere in the WCD system. Preferred locations are near electronic components whose content may become updated, such as processors, memories and the like. Accordingly, in FIG. 1, NFC tag 191 is provided within external defibrillator 100, which is also sometimes called a security NFC tag 191.

In FIG. 1, an accessing device 141 is shown, which is communicating with external defibrillator 100. Accessing device 141 may be a programmer for defibrillator 100, an accessory for WCD system, a peripheral, a base station configured to receive action data generated by and stored in a memory of defibrillator 100, a computer, a generic communication device such as a mobile smartphone, a laptop, a tablet with suitable applications loaded, and so on. Accessing device 141 may include a peripheral processor, an Accessing Wireless Communication Module (AWCM), and a Near Field Communications (NFC) reader that can communicate with NFC tag 191. In addition, and depending on its construction, accessing device 141 may include a user interface with input and output devices, such as a keyboard, a touchscreen, buttons and other actuators, a microphone, a speaker, and so on.

In this example, it should be observed that there are two communication links (comlinks) established between accessing device 141 and defibrillator 100, namely RFID comlink 198 and data comlink 148. It should also be observed that, in FIG. 1, distances are not necessarily drawn to scale; indeed, accessing device 141 may be much closer to defibrillator 100 for comlinks 198, 148 to be established, than is suggested by the drawing taking into account the dimensions of patient 82. Moreover, comlinks 198, 148 may be established and used at times that patient 82 is not wearing support structure 170, or any other component of the WCD system.

NFC tag 191 may be used to help pair accessing device 141 with external defibrillator 100. External defibrillators benefit from connecting with other devices for the purposes of receiving configuration data and updates, and downloading data.

For patient safety reasons, it is very important to prevent or avoid mistakes of the type that a peripheral might connect to the wrong defibrillator. Such risks are enhanced when these connections are wireless. In embodiments, such risks are mitigated by using NFC tags to pair the components that would communicate. In embodiments or versions, NFC tag 191 is capable of storing connectivity and security data for defibrillator 100. Accessing device 141 would read this connectivity and security data as keys for knowing how to connect to specific defibrillator 100. Because NFC technology requires the tag and reader to be within very close proximity, the user can thus be reasonably certain that the correct defibrillator is being connected to the peripheral.

A prior art defibrillator typically decides whether to defibrillate or not based on an ECG signal of the patient. However, external defibrillator 100 may initiate defibrillation (or hold-off defibrillation) based on a variety of inputs, with ECG merely being one of them.

Accordingly, it will be appreciated that signals such as physiological signals containing physiological data are obtained from patient 82. While the patient may be a considered also a "user" of the WCD system, this is not a requirement. That is, for example, a user of the wearable cardioverter defibrillator (WCD) may include a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document. Device 180 may include one or more sensors or transducers that are configured to render one or more physiological inputs from one or more patient parameters that it senses.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this description.

Figure 2:
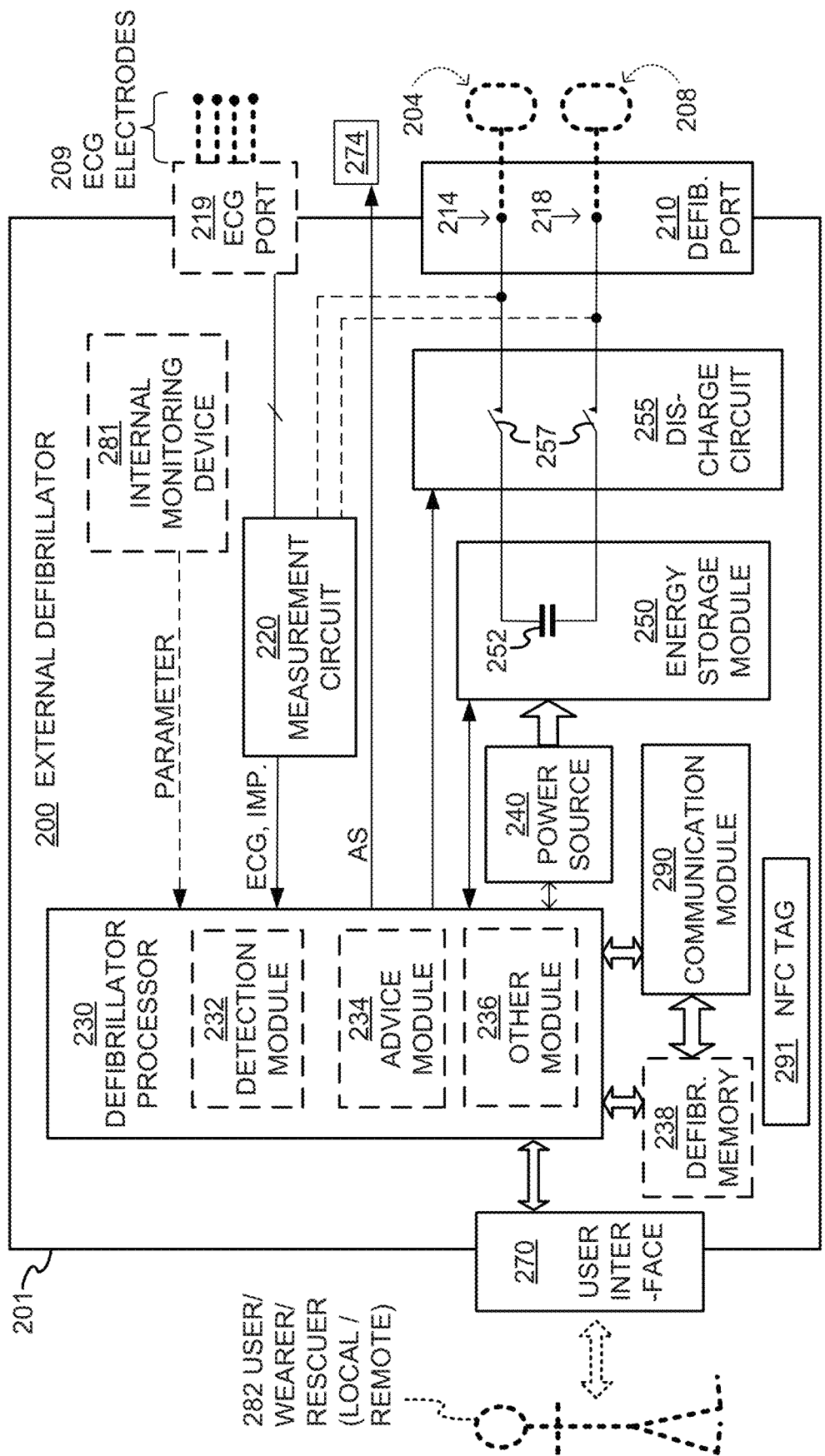
FIG. 2 is a diagram showing sample components of an external defibrillator, such as the one belonging in the WCD system of FIG. 1, and which includes an NFC tag according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 270 for a user 282. User 282 can be patient 82, also known as wearer 82. Or user 282 can be a local rescuer at the scene, such as a bystander who might offer assistance, or a trained person. Or, user 282 might be a remotely located trained caregiver in communication with the WCD system.

User interface 270 can be made in any number of ways. User interface 270 may include output devices, which can be visual, audible or tactile, for communicating to a user. For example, an output device can be a light, or a screen to display what is sensed, detected and/or measured, and provide visual feedback to rescuer 282 for their resuscitation attempts, and so on. Another output device can be a speaker, which can be configured to issue voice prompts, etc. Sounds, images, vibrations, and anything that can be perceived by user 282 can also be called human perceptible indications. User interface 270 may also include input devices for receiving inputs from users. Such input devices may additionally include various controls, such as pushbuttons, keyboards, touchscreens, a microphone, and so on. An input device can be a cancel switch, which is sometimes called a "live-man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the system parameters are to be monitored by which monitoring device can be done according to design considerations. Device 281 may include one or more transducers that are configured to render one or more physiological inputs from one or more patient parameters that it senses. Of course, device 281 is provided above and beyond ECG port 219.

Patient physiological parameters include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, the monitoring device may include one or more sensors configured to acquire patient physiological signals. Examples of such sensors include electrodes to detect ECG data, a perfusion sensor, a pulse oximeter, a Doppler device for detecting blood flow, a cuff for detecting blood pressure, an optical sensor, illumination detectors and perhaps sources for detecting color change in tissue, a motion sensor, a device that can detect heart wall movement, a sound sensor, a device with a microphone, an $SpO_2$ sensor, and so on. It will be appreciated that such sensors can help detect the patient's pulse, and can therefore also be called pulse detection sensors, pulse sensors, and pulse rate sensors. Pulse detection is also taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 282. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$ or $CO_2$; f) respiratory function, respiratory rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be configured to detect a motion event. In response, the motion detector may render or generate from the detected motion event a motion detection input that can be received by a subsequent device or functionality. A motion event can be defined as is convenient, for example a change in motion from a baseline motion or rest, etc. Such a motion detector can be made in many ways as is known in the art, for example by using an accelerometer. In such cases, the patient parameter is a motion, the transducer includes a motion detector, and the physiological input is a motion measurement.

System parameters of a WCD system can include system identification, battery status, system date and time, reports of self-testing, records of data entered, records of episodes and intervention, and so on.

Environmental parameters can include ambient temperature and pressure. A humidity sensor may provide information as to whether it is likely raining. Presumed patient location could also be considered an environmental parameter. The patient location could be presumed if monitoring device 180 or 281 includes a GPS location sensor as per the above.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in energy storage module 250. The electric charge will be the shock for defibrillation, pacing, and so on.

Defibrillator 200 may optionally also have an ECG port 219 in housing 201, for plugging in sensing electrodes 209, which are also known as ECG electrodes and ECG leads. It is also possible that sensing electrodes 209 can be connected continuously to ECG port 219, instead. Sensing electrodes 209 are types of transducers that can help sense an ECG signal, e.g. a 12-lead signal, or a signal from a different number of leads, especially if they make good electrical contact with the body of the patient. Sensing electrodes 209 can be attached to the inside of support structure 170 for making good electrical contact with the patient, similarly as defibrillation electrodes 204, 208.

Optionally a WCD system according to embodiments also includes a fluid that it can deploy automatically between the electrodes and the patient skin. The fluid can be conductive, such as by including an electrolyte, for making a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away, after it has been deployed. The fluid can be used for both defibrillation electrodes 204, 208, and sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated responsive to receiving activation signal AS from processor 230, prior to the electrical discharge.

In some embodiments, defibrillator 200 also includes a transducer that includes a measurement circuit 220. Measurement circuit 220 senses one or more electrical physiological signal of the patient from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the physiological input reflects an ECG measurement. The parameter can be an ECG, which can be sensed as a voltage difference between electrodes 204, 208. In addition the parameter can be an impedance, which can be sensed between electrodes 204, 208 and/or the connections of ECG port 219. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 also includes a processor 230, which is also known defibrillator processor. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 230 may include, or have access to, non-volatile memory for storage of machine readable and machine executable instructions. The instructions, which may also referred to as "software," generally provide for functionality by performing methods as may be disclosed herein or understood by one skilled in the art in view of the disclosed embodiments. In some embodiments, and as a matter of convention used herein, instances of the software may be referred to as a "module" and by other similar terms. Generally, where introduced as a module, the instruction set is provided to offer or fulfill a particular functionality. Embodiments of modules and the functionality delivered are not limited by the embodiments set forth herein.

Processor 230 can be considered to have a number of modules. One such module can be a detection module 232. Detection module 232 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more of ECG signals that are captured according to embodiments, and determining whether a shock criterion is met. The determination can be made from a rhythm analysis of the captured ECG signal or otherwise.

In some embodiments, when the determination is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can also be called defibrillator memory 238. Memory 238 can work together with processor 230, for example as described above. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. The data can include patient data, system data and environmental data, for example as learned by internal monitoring device 281 and outside monitoring device 180. The data can be stored in memory 238 before it is transmitted out of defibrillator 200, or stored there after it is received by defibrillator 200.

In embodiments, defibrillator 200 may further includes an NFC tag 291. Tag 291 may be similar to tag 191, and more detailed embodiments are described later in this document.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy storage capacitor, and so on. In some embodiments, power source 240 is controlled by processor 230. Appropriate components may be included to provide for charging or replacing power source 240.

Defibrillator 200 additionally includes an energy storage module 250, which can thus be coupled to the support structure of the WCD system. Module 250 is where some electrical energy can be stored temporarily in the form of an electrical charge, when preparing it for discharge to administer a shock. In embodiments, module 250 can be charged from power source 240 to the right amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 270.

Defibrillator 200 can optionally include a communication module 290, which is also known as a Defibrillator Wireless Communication Module (DWCM) 290. DWCM 290 can be configured to establish one or more wireless communication links with other devices such as accessing device 141, which may belong to entities such as a remote assistance center, Emergency Medical Services (EMS), and so on. Module 290 may also include an antenna, portions of a processor, and other sub-components as may be deemed necessary by a person skilled in the art. This way, data and commands can be communicated, such as patient data, event information, therapy attempted, CPR performance, system data, environmental data, and so on. In addition, communication modules may be provided for wired communication with other components, peripherals, etc.

Defibrillator 200 can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since the patients' bodies differ from one another. Of course, such parameters can be stored in a memory of the WCD system, for example by accessing device 141, and so on.

A programming interface can be made according to embodiments, which receives such measured baseline physiological parameters. Such a programming interface may input automatically in the WCD system the baseline physiological parameters, along with other data.

Figure 3:
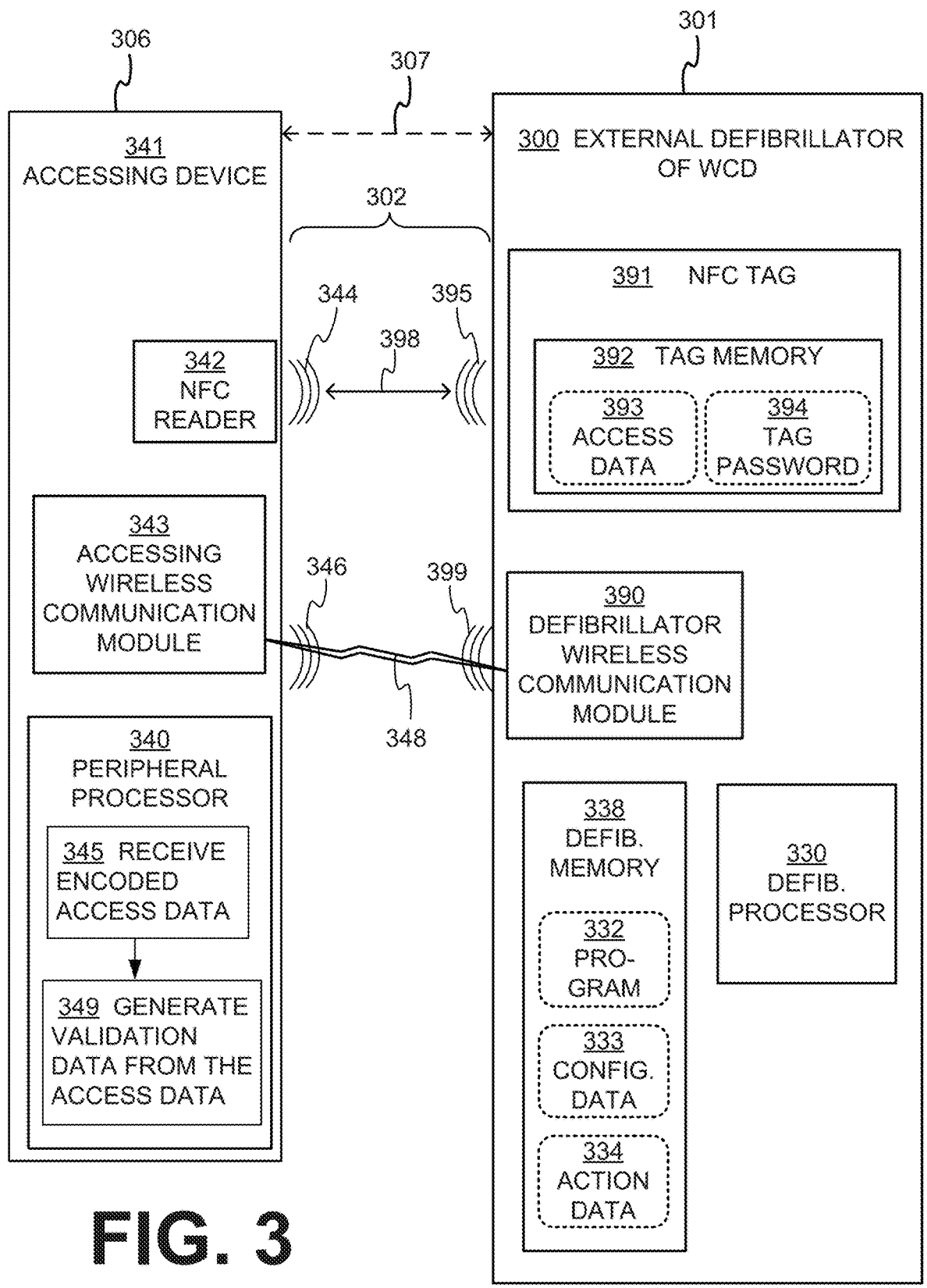
FIG. 3 is a diagram of sample components of an external defibrillator, such as the one of FIG. 2 and made according to embodiments, and also of components of an accessing device, during wireless communication between the external defibrillator and the accessing device.

FIG. 3 is a diagram of sample components of an external defibrillator 300, such as the one of FIG. 2 and made according to embodiments, and also of components of an accessing device 341, such as the one of FIG. 1, during wireless communication between external defibrillator 300 and accessing device 341.

External defibrillator 300 includes a defibrillator housing 301, which contains therein components as shown for this example. Defibrillator 300 thus includes a defibrillator processor 330, a defibrillator memory 338, a Defibrillator Wireless Communication Module (DWCM) 390 and an NFC tag 391, all of which could be made as described earlier for defibrillator processor 230, defibrillator memory 238, communication module 290 and NFC tag 291, respectively. NFC tag 391 may have a tag memory 392, which stores access data 393, and optionally also a tag password 394. Access data 393 may be needed for accessing DWCM 390.

Defibrillator memory 338 can be configured to store at least one program 332 and configuration data 333. Defibrillator processor 330 can be configured to run program 332 according to stored configuration data 333 so as to generate a decision to shock or not shock. The decision can be generated, for example, from advice module 234 plus other inputs. Over the course of time, multiple such decisions may be made, such as a first decision, a second decision, and so on.

Defibrillator processor 330 can be further configured to control the discharge circuit of the WCD system to thus discharge the electrical charge, responsive to the generated decision. Of course, if updated configuration data ever becomes stored in defibrillator memory 338 in lieu of configuration data 333, then defibrillator processor 330 can run program 332 according to such stored updated configuration data instead for generating subsequent decisions. Alternately, if an updated program ever becomes stored in defibrillator memory 338 in lieu of program 332, then defibrillator processor 330 can run the updated program according to configuration data 333 or according to any stored updated configuration data, for generating subsequent decisions.

Defibrillator memory 338 can be configured to further store action data 334. Action data 334 may have been generated by operation of the WCD system, and include historical data of the patient, of operations and events, notifications, and so on.

Accessing device 341 may be a defibrillator configurator, of the type that clinicians use. Accessing device 341 may be used for purposes such as providing software updates, updated configuration data for configuration settings for this specific WCD, for a specific patient, and so on. Accessing device 341 includes a peripheral housing 306, which contains therein components as shown. Accessing device 341 includes at least an NFC reader 342, a peripheral processor 340 and an Accessing Wireless Communication Module (AWCM) 343. It may also have a user interface, and so on.

External defibrillator 300 can be configured to wirelessly exchange data with accessing device 341. The wireless exchange may happen over RFID comlink 398 and data comlink 348, which can be as comlinks 198, 148. Comlinks 398, 348 can be characterized as taking place over an air interface 302.

For RFID comlink 398, NFC reader 342 can be configured to transmit a wireless interrogation wave 344. NFC tags work by using RFID principles, for example NFC tag 391 may harness energy wirelessly from NFC reader 342. NFC tag 391 can be configured to receive interrogation wave 344 from NFC reader 342, and to transmit wirelessly a backscatter wave 395 responsive to the received interrogation wave 344. Since NFC technology is being used, these exchanges over RFID comlink 398 may not happen over large distances, thus better preventing the wrong WCD systems from being programmed. In fact, when NFC tag 391 receives wireless interrogation wave 344 from NFC reader 342 and transmits wirelessly backscatter wave 395, peripheral housing 306 is at a short distance from NFC tag 391. Peripheral housing 306 has a distance 307 from defibrillator housing 301. If, as is preferred, NFC tag 391 is provided within defibrillator housing 301, then distance 307 is short, may be at most 10", and in practice around 1" or less.

Backscatter wave 395 may encode access data 393, and be received by NFC reader 342 of accessing device 341. In some embodiments, given that access data 393 is thus learned by accessing device 341, peripheral processor 340 may generate validation data for addressing DWCM 390. More particularly, as shown within peripheral processor 340, according to an operation 345, encoded access data 393 is received. According to a subsequent operation 349, validation data is generated from the received encoded access data 393. This validation data may thus be generated from encoded access data 393 that was backscattered by NFC tag 391 and received by NFC reader 342. This validation data may include access data 393, a hash of access data 393, and so on. It may include a network address of the DWCM, keys for addressing DWCM 390, and the like. If the validation data is exactly the same as access data, then operation 349 need not take place other than to store locally the access data at least temporarily before transmitting it.

Various measures may be taken to protect access data 393, while it is being backscattered. First, since this NFC tag already uses RFID-type technology at low power, a threat might be only from listeners at a very close range, which is a factor that may be controlled. Second, the backscattered encoded access data may be encrypted. Third, NFC tag 391 may be readable only via a password. For example, tag memory 392 can be further configured to store a tag password 394; plus, NFC tag 391 can be configured to not backscatter encoded access data 393 unless interrogation wave 344 also encodes tag password 394. In such embodiments, the WCD system may have been assigned a serial number, and tag password 394 can that serial number, or be related to that serial number. In such cases, the serial number could be used to ensure that the specific accessing device (e.g., a Defibrillator Configurator) has permission to connect with that particular defibrillator. This may be accomplished by supplying the serial number to a secure website where the user has been authenticated, and has granted permission that appropriate security keys are given to devices for communicating with the WCD system. Accordingly, the NFC tag would store unique data pertaining to only this defibrillator on this particular patient. It is possible that only a defibrillator configurator that has been given the necessary security data for one particular defibrillator on a particular patient would be allowed to connect. This creates another layer of security that prevents rogue defibrillator configurators from being able to attack maliciously defibrillator 300.

An advantage of embodiments is that DWCM 390 need not transmit its keys or network address to any interrogating peripheral. In particular, DWCM 390 can be assigned a network address, and not transmit that network address in response to a query signal by AWCM 343. In fact, DWCM 390 may remain silent unless properly addressed, not broadcasting its presence, address, or anything else. Other devices won't even know that the nearby DWCM 390 has a wireless connection, until the NFC tag is read successfully.

In embodiments, AWCM 343 may properly address defibrillator 300, and its DWCM 390, by transmitting the validation data it generated at operation 349. This may take place within data comlink 348. AWCM may further transmit, in a wave 346, updated configuration data, an updated program such a software update or a software patch, or a request for a memory download.

DWCM 390 may cooperate with defibrillator processor 330. DWCM 390 may receive wave 346 what the AWCM transmitted, and with it the validation data. If it is determined that the received validation data has been generated from the backscattered encoded access data 393, then defibrillator processor 330 may react accordingly. For example, defibrillator processor 330 can be further configured to cause DWCM 390 to transmit a reply wave 399, with an acknowledgement, for establishing data comlink 348.

Data comlink 348 can be established in a number of ways, and using a number of wireless protocols. On such sample protocol is WiFi. NFC tag 391 could store an IP address, SSID, and password. This data would be used to set up the secure WiFi network. Disconnection from the network by either side could bring down the WiFi network, in which case the NFC tag would need to be read again, in case the accessing device 341 would not store this data. The data on the NFC tag could also be encrypted with a symmetric or asymmetric key, to protect against malicious users attempting to read the information.

Another such sample protocol is Bluetooth. NFC tag 391 could contain a MAC address and a security key. This information would be used for accessing device 341 to pair or connect with defibrillator 300. In some embodiments, when the two devices become unpaired or disconnected, neither device would store data about the pairing to allow repairing. NFC tag 391 would need to be read again in order to pair or connect new devices. Again, data on NFC tag 391 could also be encrypted with a symmetric or asymmetric key, to protect against malicious users attempting to read the information.

In some embodiments, if wave 346 encodes updated configuration data, defibrillator processor 330 can be further configured to store in defibrillator memory 338 the received updated configuration data in lieu of configuration data 333. Such can be both for configuration data being initially received, and also for updates. When configuration data is initially received, it is possible that there was no configuration data had been stored, or standard configuration data had been stored. In such cases, defibrillator processor 330 is configured to store in the defibrillator memory the received configuration data, and the defibrillator processor thus becomes configured to run the program according to the stored configuration data so as to generate a certain decision to shock or not shock, and to control the discharge circuit to thus discharge the electrical charge responsive to the certain decision being to shock. When the received configuration data is an update, this means that defibrillator memory 338 further stored previous configuration data, and defibrillator processor 330 was configured to run program 332 according to the stored previous configuration data so as to generate a previous decision to shock or not shock. Defibrillator processor 330 was further configured to control the discharge circuit to thus discharge the electrical charge responsive to the previous decision being to shock.

In some embodiments, if wave 346 encodes an updated program, defibrillator processor 330 can be further configured to store in defibrillator memory 338 the received updated program in lieu of program 332. Such can be both for a program being initially received, and also for updates being installed. Such WCD systems use the security NFC tag for uploading software.

In some embodiments, if wave 346 encodes a request for a memory download, defibrillator processor 330 can be further configured to cause action data 334 to be encoded in reply wave 399. Such WCD systems use the security NFC tag to enable requests of data from the memory.

Examples are now described. The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs. Methods are now described.

In some embodiments, configuration data is uploaded and stored in the WCD system for use. Examples of such uploading are now described in conjunction with FIGS. 3, 4 and 5.

Figure 4:
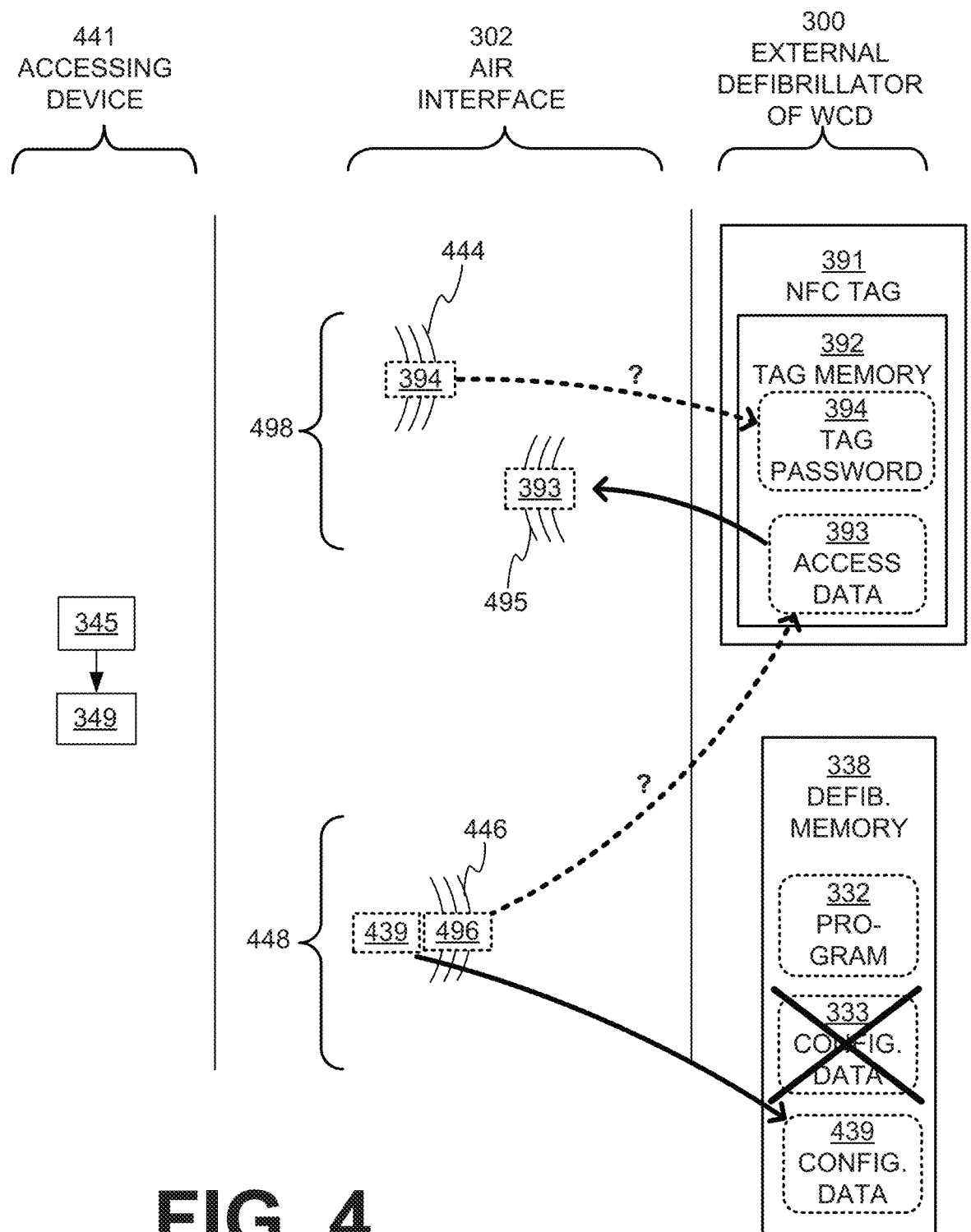
FIG. 4 is a diagram of sample operations occurring when configuration data is being uploaded to the external defibrillator of FIG. 3 according to embodiments.

FIG. 4 is a diagram of sample operations occurring when configuration data is being uploaded to external defibrillator 300 of FIG. 3. The upload may take place from an accessing device 441, which can be as described previously for accessing devices 341.

For example, accessing device 441 can be configured to perform the previously described operations 345, 349. It can also establish comlinks 498, 448 similar to comlinks 398, 348 via air interface 302.

Figure 5:
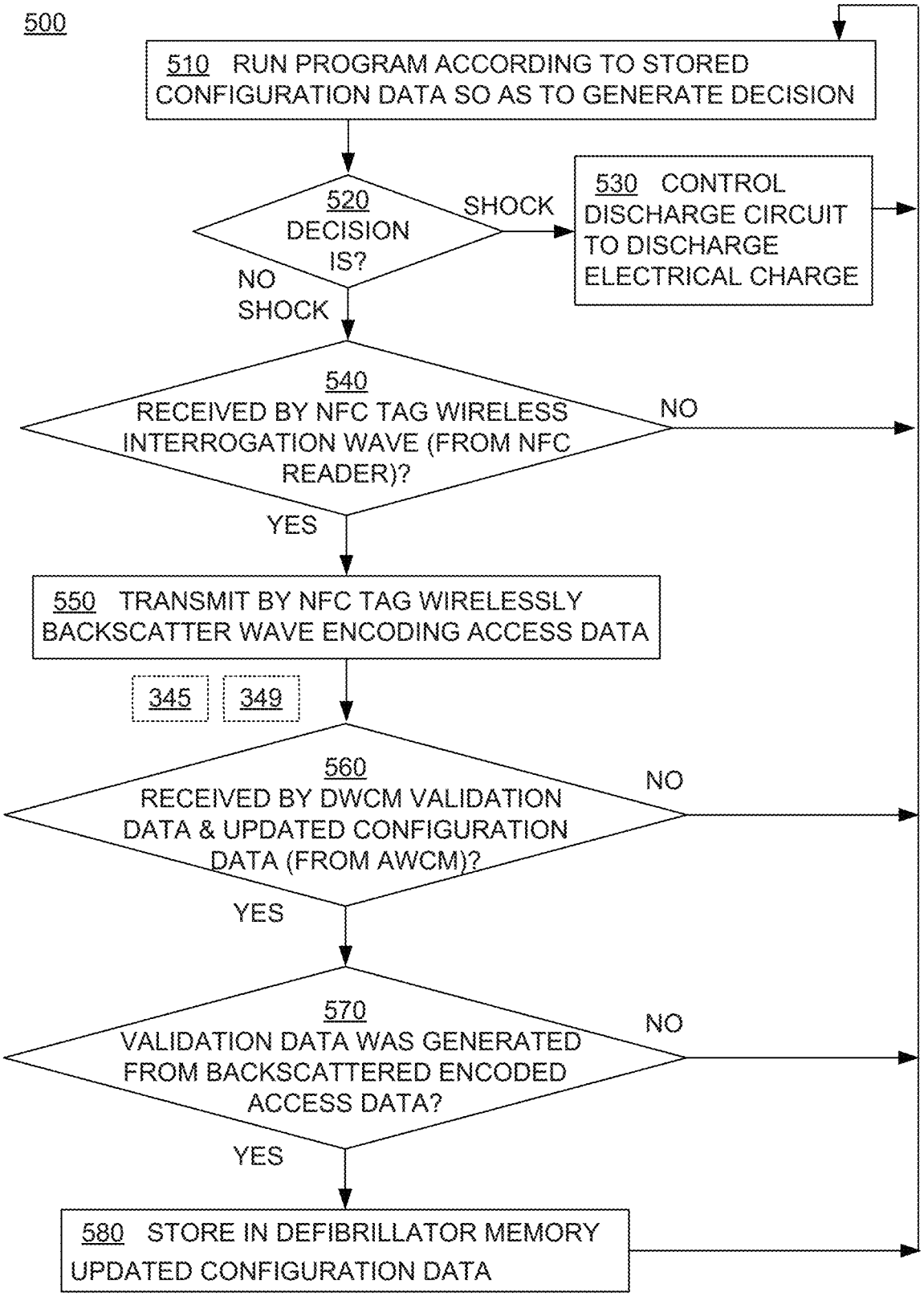
FIG. 5 is a flowchart for illustrating methods for the external defibrillator of FIG. 3 according to embodiments where the operations of FIG. 4 are being performed.

FIG. 5 shows a flowchart 500 for describing methods according to embodiments. According to an operation 510, a defibrillator processor may run a program according to stored configuration data, so as to generate a first decision to shock or not shock. In subsequent times operation 510 is run, a second decision may be generated, and so on. Sometimes such a decision may be characterized as previous, for example if it is made by previous configuration data, and so on.

According to another operation 520, it is determined what the decision of operation 510 was. If the decision were to shock then, according to another operation 530, the discharge circuit may be controlled by the defibrillator processor to discharge the electrical charge as has been described above. Then execution may return to operation 510.

If at operation 520 the decision is to not shock then, according to another operation 540, it is determined whether a wireless interrogation wave from an NFC reader was received by NFC tag 391. The NFC reader could be NFC reader 342. If not, then execution may return to operation 510.

A situation where a wireless interrogation wave 444 was indeed received can be seen in FIG. 4. As has been described previously, in some embodiments, interrogation wave 444 may further encode a tag password 394 of NFC tag 391. In fact, the tag password encoded by interrogation wave 444—whatever it is—will be checked against tag password 394 stored in tag memory 392 of NFC tag 391 for validity. This checking for validity is shown conceptually by a dashed line from 394 to 394 with a question mark.

Returning to FIG. 5, if a wireless interrogation wave has indeed been received at operation 540 then, according to another operation 550, a backscatter wave may be transmitted wirelessly by the NFC tag. The backscatter wave may encode access data stored in the tag memory. If a password were required for the NFC tag, then this backscattering can be configured to take place only if the valid tag password has been transmitted.

FIG. 4 shows backscatter wave 495 encoding access data 393 that is stored in tag memory 392. After that, operations 345, 349 may be performed by accessing device 441, and a wave 446 similar to wave 346 may be transmitted. As mentioned above, wave 446 may encode validation data 496 and updated configuration data 439.

Returning to FIG. 5, operations 345, 349 are shown only to indicate the sequence at which they are performed, after operation 550. These operations 345, 349 are shown in dotted lines so as to indicate that they are not part of flowchart 500.

After operation 550, according to another operation 560, it may be determined whether the validation data and the updated configuration data transmitted by the AWCM have been received wirelessly by the DWCM. If not, then execution may return to operation 510.

In some embodiments, the DWCM will wait for the validation data and the updated configuration data only for a limited time, to increase security. For example, a timeout period may start after the backscatter wave is transmitted at operation 550. The timeout period may be short, such as 1 sec. In such embodiments, the received configuration data can be stored in the defibrillator memory only if it is received by the DWCM before the timeout period expires.

If yes then, according to another operation 570, it may be determined whether or not the received validation data has been generated from the backscattered encoded access data. This operation may serve external defibrillator 300 to authenticate accessing device 441. (In FIG. 4, this authentication operation is shown conceptually by a dashed line from validation data 496 to access data 393 with a question mark.) As mentioned previously, in some embodiments the validation data is identical to the access data. In FIG. 5, at operation 570, if the answer is no, then execution may return to operation 510.

If at operation 570 the answer is yes then, according to another operation 580, the received updated configuration data may be stored by the defibrillator processor in the defibrillator memory, in response to determining that the received validation data has been generated from the backscattered encoded access data and, of course, to the fact that the received updated program was transmitted and received. Such storing can be in lieu of previous configuration data stored there. (FIG. 4 also shows that updated configuration data 439 of wave 446 becomes stored in memory 338 in lieu of previous configuration data 338.) Execution then may return to operation 510, for a second decision and so on.

In some embodiments, one or more programs are uploaded and stored in the WCD system for use. Examples of such uploading are now described in conjunction with FIGS. 3, 6 and 7.

Figure 6:
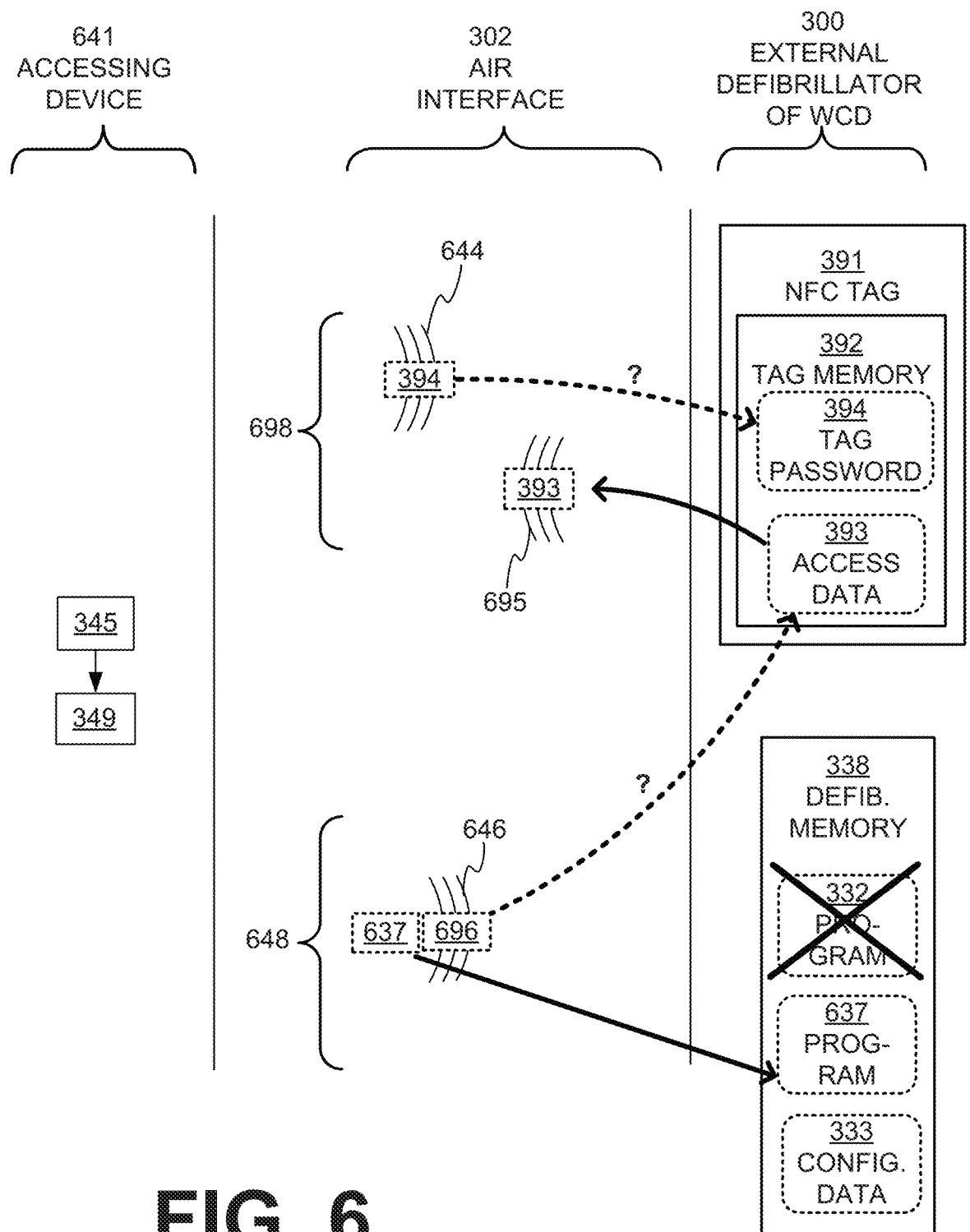
FIG. 6 is a diagram of sample operations occurring when a software update is being uploaded to the external defibrillator of FIG. 3 according to embodiments.

FIG. 6 is a diagram of sample operations occurring when a program is being uploaded to external defibrillator 300 of FIG. 3. The upload may take place from an accessing device 641, which can be as described previously for accessing devices 341. For example, accessing device 641 can be configured to perform the previously described operations 345, 349. It can also establish comlinks 698, 648 similar to comlinks 398, 348 via air interface 302.

Figure 7:
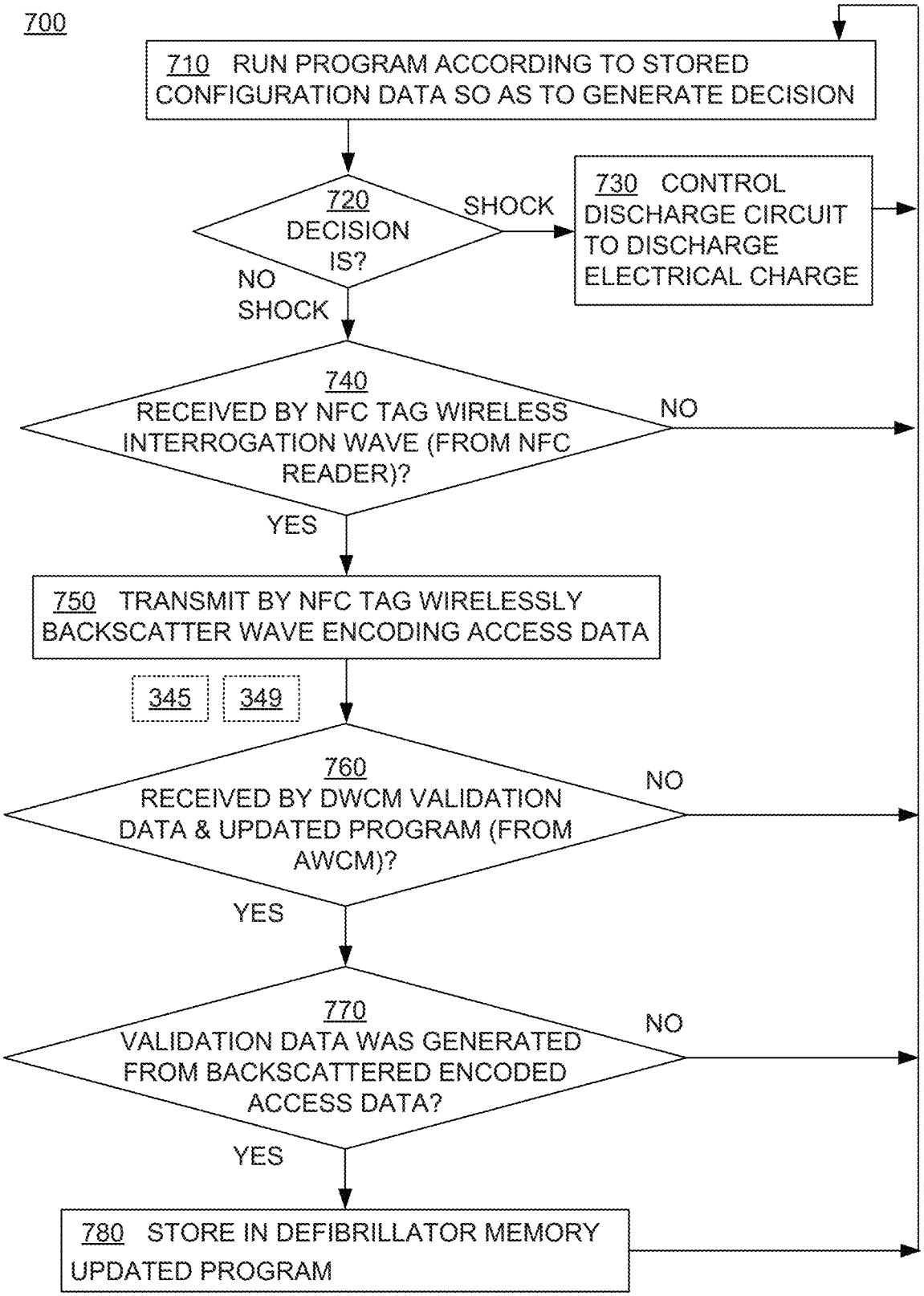
FIG. 7 is a flowchart for illustrating methods for the external defibrillator of FIG. 3 according to embodiments where the operations of FIG. 6 are being performed.

FIG. 7 shows a flowchart 700 for describing methods according to embodiments. According to an operation 710, a defibrillator processor may run a program according to stored configuration data, so as to generate a first decision to shock or not shock. In subsequent times operation 710 is run, a second decision may be generated, and so on. Sometimes such a decision may be characterized as previous, for example if it is made by a previous program, and so on.

According to another operation 720, it is determined what the decision of operation 710 was. If the decision were to shock then, according to another operation 730, the discharge circuit may be controlled by the defibrillator processor to discharge the electrical charge as has been described above. Then execution may return to operation 710.

If at operation 720 the decision is to not shock then, according to another operation 740, it is determined whether a wireless interrogation wave from an NFC reader was received by NFC tag 391. If not, then execution may return to operation 710.

A situation where a wireless interrogation wave 644 was indeed received can be seen in FIG. 6. As has been described previously, in some embodiments, interrogation wave 644 may further encode a tag password 394 of NFC tag 391. In fact, the tag password encoded by interrogation wave 644—whatever it is—will be checked against tag password 394 stored in tag memory 392 of NFC tag 391 for validity. This checking for validity is shown conceptually by a dashed line from 394 to 394 with a question mark.

Returning to FIG. 7, if a wireless interrogation wave has indeed been received at operation 740 then, according to another operation 750, a backscatter wave may be transmitted wirelessly by the NFC tag. The backscatter wave may encode access data stored in the tag memory. If a password were required for the NFC tag, then this backscattering can be configured to take place only if the valid tag password has been transmitted.

FIG. 6 shows backscatter wave 695 encoding access data 393 that is stored in tag memory 392. After that, operations 345, 349 may be performed by accessing device 641, and a wave 646 similar to wave 346 may be transmitted. As mentioned above, wave 646 may encode validation data 696 and updated program 637.

Returning to FIG. 7, operations 345, 349 are shown only to indicate the sequence at which they are performed, after operation 750. These operations 345, 349 are shown in dotted lines so as to indicate that they are not part of flowchart 700.

After operation 750, according to another operation 760, it may be determined whether the validation data and the updated program transmitted by the AWCM have been received wirelessly by the DWCM. If not, then execution may return to operation 710. As with operation 550, also for operation 750 the DWCM may wait for the validation data and the new program only for a limited time, to increase security. In such embodiments, the received program can be stored in the defibrillator memory only if it is received by the DWCM before the timeout period expires.

If at operation 750 the answer is yes then, according to another operation 770, it may be determined whether or not the received validation data has been generated from the backscattered encoded access data. This operation may serve external defibrillator 300 to authenticate accessing device 641. (In FIG. 6, this authentication operation is shown conceptually by a dashed line from validation data 696 to access data 393 with a question mark.) As mentioned previously, in some embodiments the validation data is identical to the access data. In FIG. 7, at operation 770, if the answer is no, then execution may return to operation 710.

If at operation 770 the answer is yes then, according to another operation 780, the received updated program may be stored by the defibrillator processor in the defibrillator memory, in response to determining that the received validation data has been generated from the backscattered encoded access data and, of course, to the fact that the received updated program was transmitted and received. Such storing can be in lieu of the previous program stored there. (FIG. 6 also shows that updated program 637 of wave 646 becomes stored in memory 338 in lieu of previous program 332.) Execution then may return to operation 710, for a second decision and so on.

In some embodiments, action data is downloaded and stored in the WCD system for review. Such action data may include shock/no shock decisions, inputs for running the program such as configuration data, a value of a physiological parameter of the patient that may be sensed by one of the sensors, an identifying number that has been assigned to the patient, WCD system status data such as a level of energy of the power source, and so on. Taken together, such data may amount to a history of monitoring and treating the patient. Examples of such downloading are now described in conjunction with FIGS. 3, 8 and 9.

Figure 8:
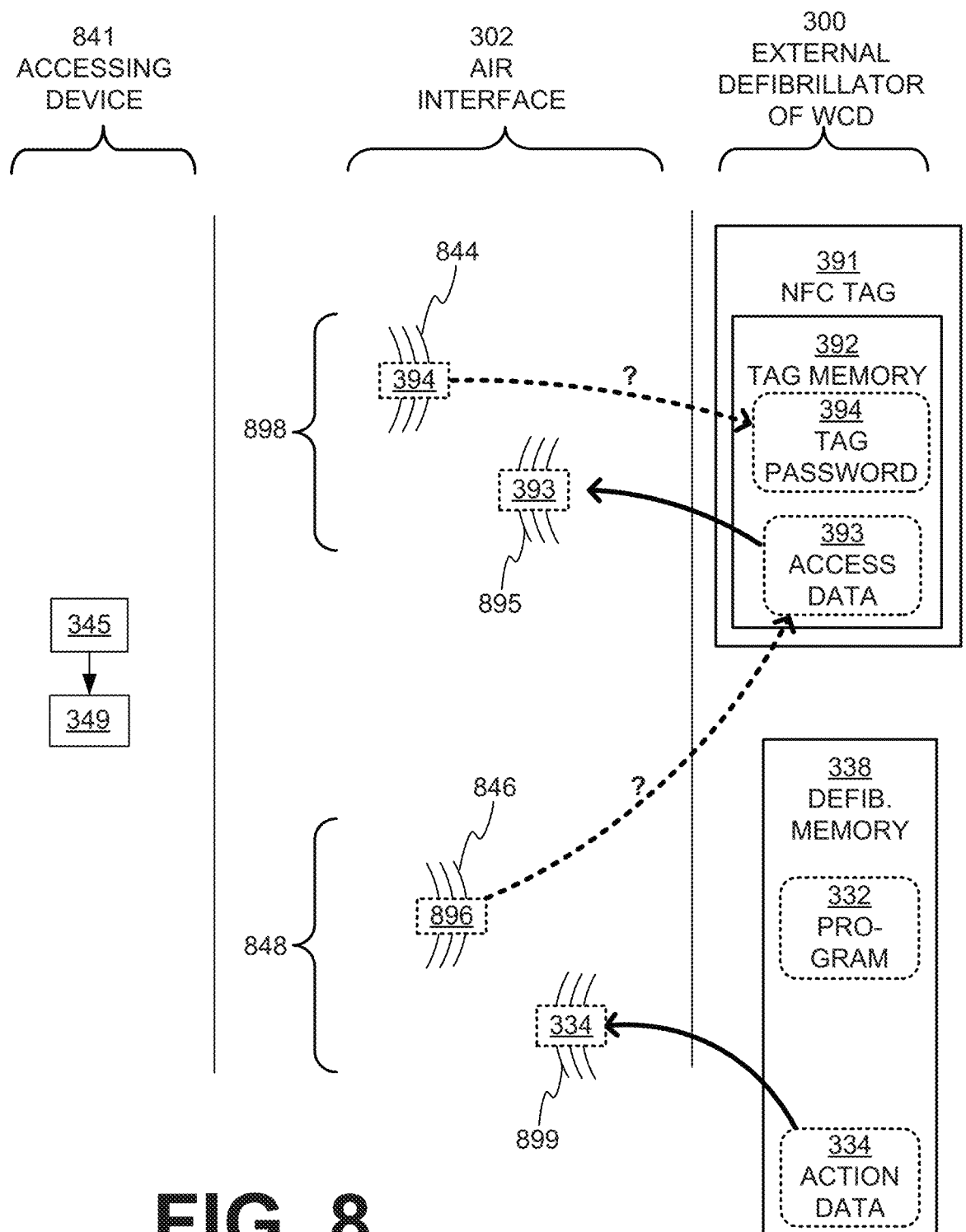
FIG. 8 is a diagram of sample operations occurring when action data of the external defibrillator of FIG. 3 is being downloaded according to embodiments.

FIG. 8 is a diagram of sample operations occurring when action data is being downloaded from external defibrillator 300 of FIG. 3. The download may take place from an accessing device 841, which can be as described previously for accessing devices 341. For example, accessing device 841 can be configured to perform the previously described operations 345, 349. It can also establish comlinks 898, 848 similar to comlinks 398, 348 via air interface 302.

Figure 9:
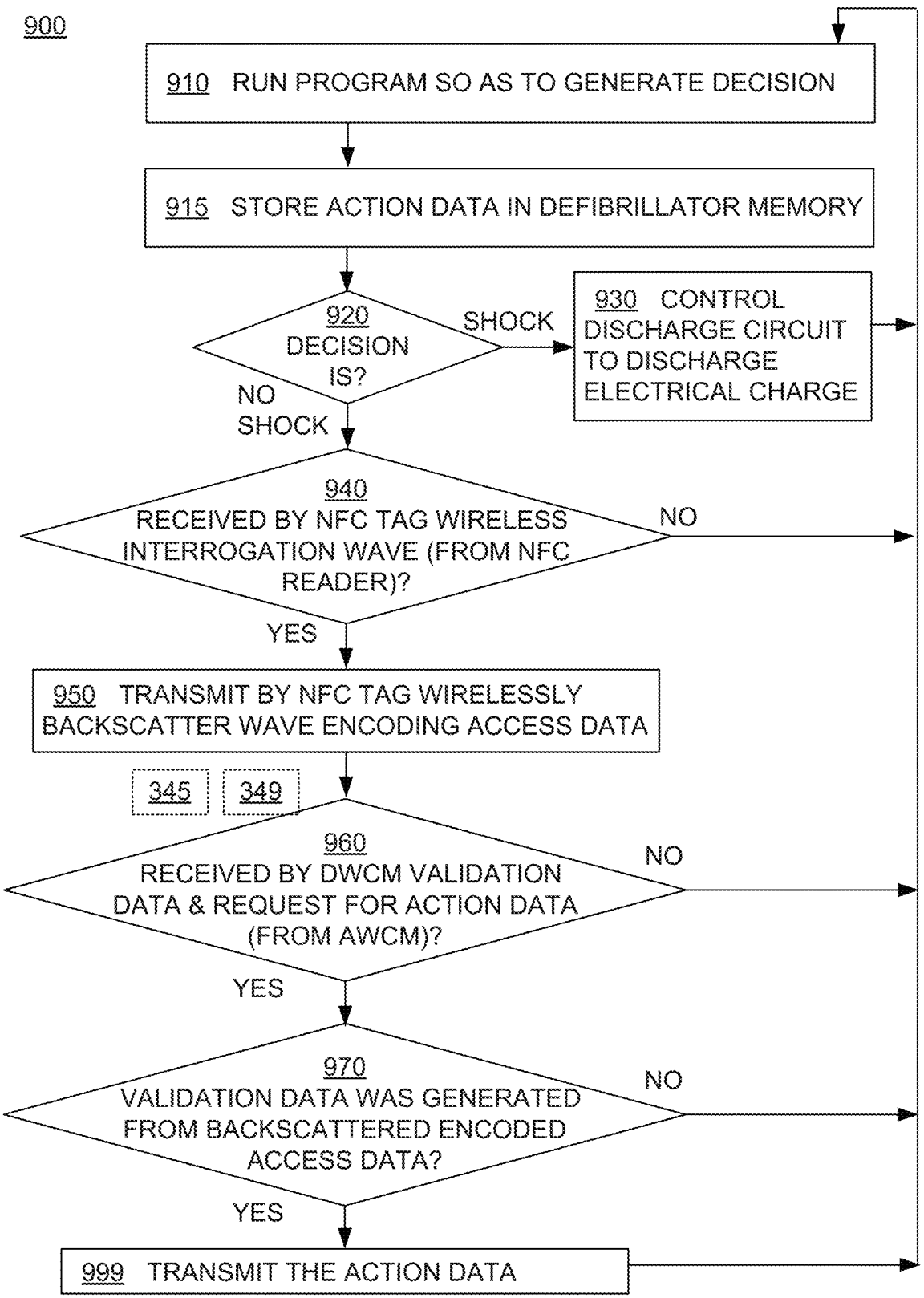
FIG. 9 is a flowchart for illustrating methods for the external defibrillator of FIG. 3 according to embodiments where the operations of FIG. 8 are being performed.

FIG. 9 shows a flowchart 900 for describing methods according to embodiments. According to an operation 910, a defibrillator processor may run a program according to stored configuration data, so as to generate a first decision to shock or not shock. In subsequent times operation 910 is run, a second decision may be generated, and so on.

According to another operation 915, action data may be stored in the defibrillator memory, which relates to at least one of the first decision and inputs for thus running the program.

According to another operation 920, it is determined what the decision of operation 910 was. If the decision were to shock then, according to another operation 930, the discharge circuit may be controlled by the defibrillator processor to discharge the electrical charge as has been described above. Then execution may return to operation 910.

If at operation 920 the decision is to not shock then, according to another operation 940, it is determined whether a wireless interrogation wave from an NFC reader was received by NFC tag 391. If not, then execution may return to operation 910.

A situation where a wireless interrogation wave 844 was indeed received can be seen in FIG. 8. As has been described previously, in some embodiments, interrogation wave 844 may further encode a tag password 394 of NFC tag 391. In fact, the tag password encoded by interrogation wave 844— whatever it is—will be checked against tag password 394 stored in tag memory 392 of NFC tag 391 for validity. This checking for validity is shown conceptually by a dashed line from 394 to 394 with a question mark.

Returning to FIG. 9, if a wireless interrogation wave has indeed been received at operation 940 then, according to another operation 950, a backscatter wave may be transmitted wirelessly by the NFC tag. The backscatter wave may encode access data stored in the tag memory. If a password were required for the NFC tag, then this backscattering can be configured to take place only if the valid tag password has been transmitted.

FIG. 8 shows backscatter wave 895 encoding access data 393 that is stored in tag memory 392. After that, operations 345, 349 may be performed by accessing device 841, and a wave 846 similar to wave 346 may be transmitted. As mentioned above, wave 846 may encode validation data 896 and a request for action data 334.

Returning to FIG. 9, operations 345, 349 are shown only to indicate the sequence at which they are performed, after operation 950. These operations 345, 349 are shown in dotted lines so as to indicate that they are not part of flowchart 900.

After operation 950, according to another operation 960, it may be determined whether the validation data and the request transmitted by the AWCM have been received wirelessly by the DWCM. If not, then execution may return to operation 910. As with operation 550, also for operation 950 the DWCM may wait for the validation data and the new program only for a limited time, to increase security. In such embodiments, the request can be honored only if it is received by the DWCM before the timeout period expires.

If at operation 950 the answer is yes then, according to another operation 970, it may be determined whether or not the received validation data has been generated from the backscattered encoded access data. This operation may serve external defibrillator 300 to authenticate accessing device 841. (In FIG. 8, this authentication operation is shown conceptually by a dashed line from validation data 896 to access data 393 with a question mark.) As mentioned previously, in some embodiments the validation data is identical to the access data. In FIG. 9, at operation 970, if the answer is no, then execution may return to operation 910.

If at operation 970 the answer is yes then, according to another, operation 999 at least a portion of action data 334 can be transmitted wirelessly by the DWCM, in response to the request and in response to determining that the received validation data has been generated from the backscattered encoded access data. (FIG. 8 also shows a reply wave 899, similar to wave 399, encoding action data 334.) Execution then may return to operation 910, for a second decision and so on.

Tag memory 392 of NFC tag 391 may be programmed in different ways. Sample such ways are now described.

Figure 10:
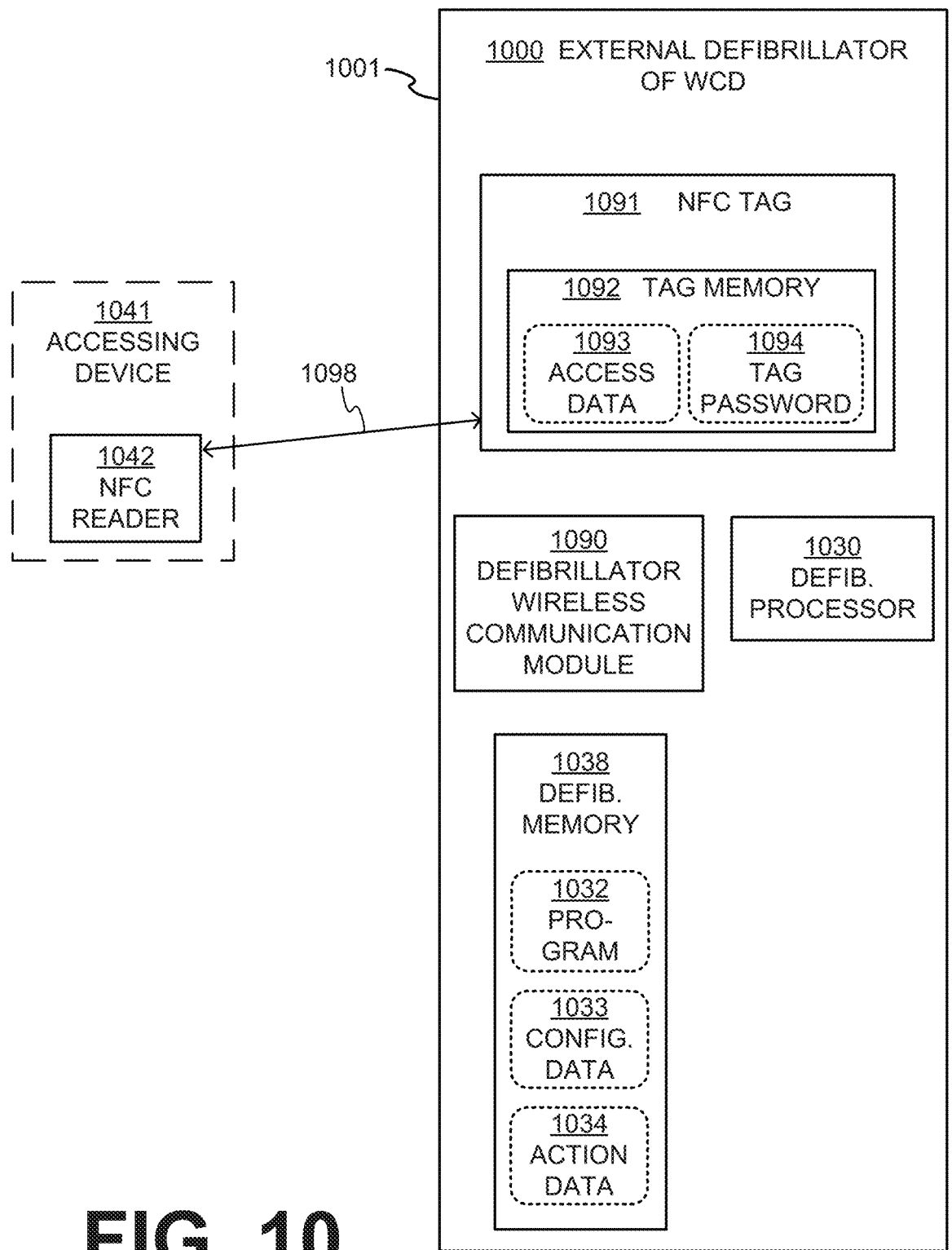
FIG. 10 is a diagram showing sample components of an external defibrillator, such as the external defibrillator of FIG. 3, in embodiments where the NFC tag receives and stores updated data directly from a trusted NFC reader.

FIG. 10 is a diagram of sample components of an external defibrillator 1000, such as the one of FIG. 2 and made according to embodiments. FIG. 10 further shows a trusted NFC reader 1042 that can be used to program NFC tag 1091 by establishing an RFID comlink 1098.

External defibrillator 1000 includes a defibrillator housing 1001, which contains therein components as shown for this example. Defibrillator 1000 thus includes a defibrillator processor 1030, a defibrillator memory 1038, a defibrillator wireless communication module (DWCM) 1090 and an NFC tag 1091, all of which could be made as described earlier for similar components of FIG. 3. Similarly, NFC tag 1091 may have a tag memory 1092, which stores access data 1093, and optionally also a tag password 1094. Access data 1093 may be needed for accessing DWCM 1090. Moreover, defibrillator memory 1038 can be configured to store at least one program 1032, and configuration data 1033 and action data 1034.

In some embodiments, NFC reader 1042 is the NFC reader of an accessing device 1041, which can be as described for accessing device 341. In this application, accessing device 1041 is being used as a programming device. In other embodiments, however, NFC reader 1042 is simply an other NFC reader, which is used solely for programming NFC tag 1091, and unrelated to accessing device 1041. For example, NFC reader 1042 could be a standalone device, which is why accessing device 1041 is shown in dashed lines in FIG. 10.

In such embodiments, NFC reader 1042 may transmit an other wireless interrogation wave that encodes updated tag data. It is understood that this updated tag data could be even the initial tag data that is intended to be stored in tag memory 1092. In such embodiments, NFC tag 1091 can be configured to receive the other wireless interrogation wave, to decode the updated tag data from the other wireless interrogation wave, and to store the updated tag data in tag memory 1092. This updated tag data may include access data and/or a tag password, which can be stored in lieu of the existing access data and/or a tag password.

Figure 11:
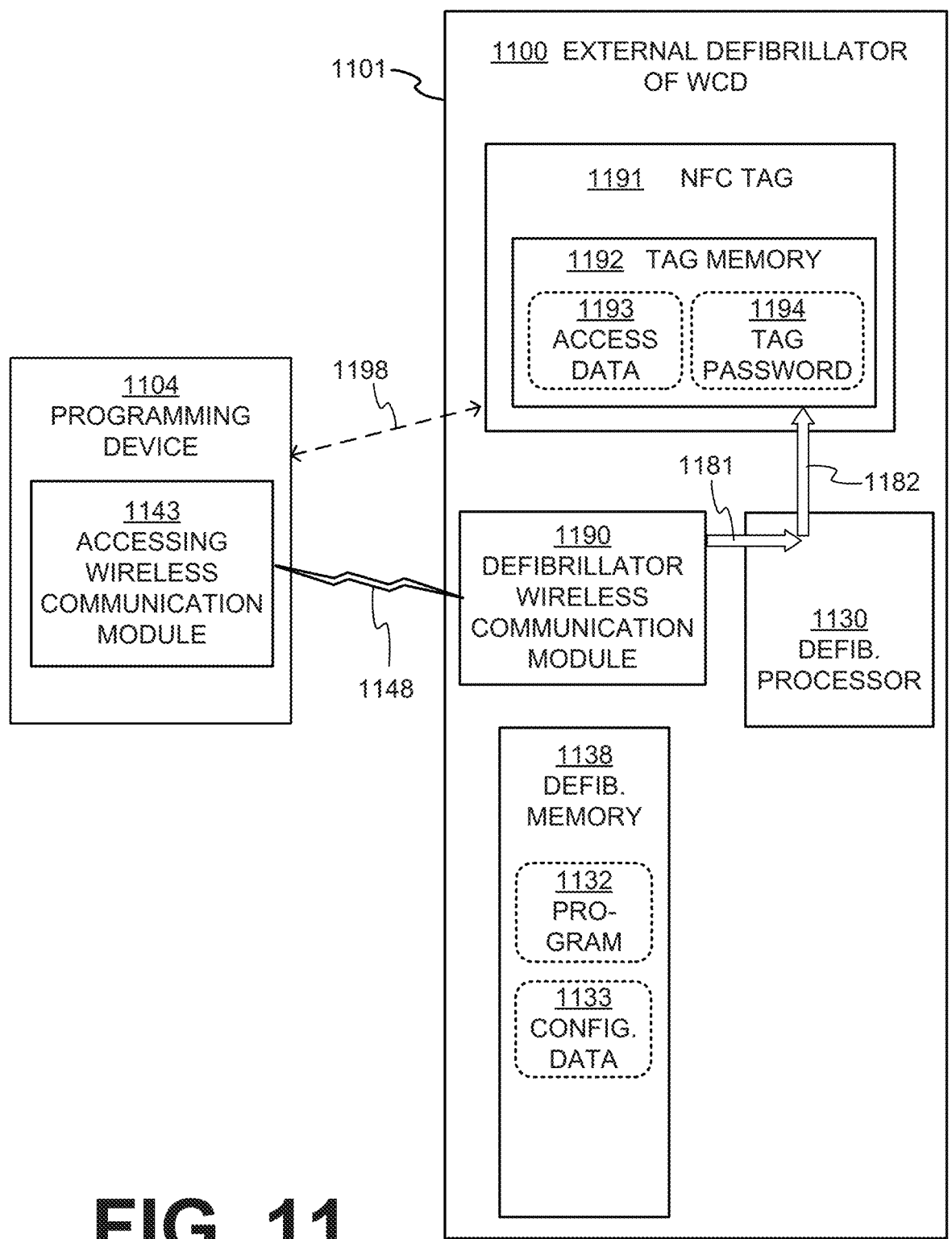
FIG. 11 is a diagram showing sample components of an external defibrillator, such as the external defibrillator of FIG. 3, in embodiments where the NFC tag receives and stores updated data directly from a trusted programming device.

FIG. 11 is a diagram of sample components of an external defibrillator 1100, such as the one of FIG. 2 and made according to embodiments. FIG. 11 further shows a trusted programming device 1104 that can be used to program NFC tag 1191.

External defibrillator 1100 includes a defibrillator housing 1101, which contains therein components as shown for this example. Defibrillator 1100 thus includes a defibrillator processor 1130, a defibrillator memory 1138, a defibrillator wireless communication module (DWCM) 1190 and an NFC tag 1191, all of which could be made as described earlier for similar components of FIG. 3. Similarly, NFC tag 1191 may have a tag memory 1192, which stores access data 1193, and optionally also a tag password 1194. Access data 1193 may be needed for accessing DWCM 1190. Moreover, defibrillator memory 1138 can be configured to store at least one program 1132 and configuration data 1133.

In some embodiments, programming device 1104 is as described for accessing device 341. Programming device 1104 may include an AWCM 1143, which can be as AWCM 343. As such, programming device 1104 may establish a data comlink 1148 with NFC tag 1191. Programming device 1104 may further optionally include an NFC reader, and as such may establish an optional RFID comlink 1198 with NFC tag 1191.

In such embodiments, AWCM 1143 may transmit wirelessly updated tag data. This updated tag data could be even the initial tag data that is intended to be stored in tag memory 1192. In such embodiments, DWCM 1190 can be further configured to receive wirelessly from the AWCM the transmitted updated tag data. This updated tag data may include access data and/or a tag password, which can be stored in tag memory 1192 in lieu of the existing access data and/or a tag password. More particularly, defibrillator processor 1130 can be further configured to store the received updated tag data in tag memory 1192. In some embodiments, the path of the updated tag data for this updating operation can be shown in FIG. 11 by two arrows 1181, 1182.

Figure 12:
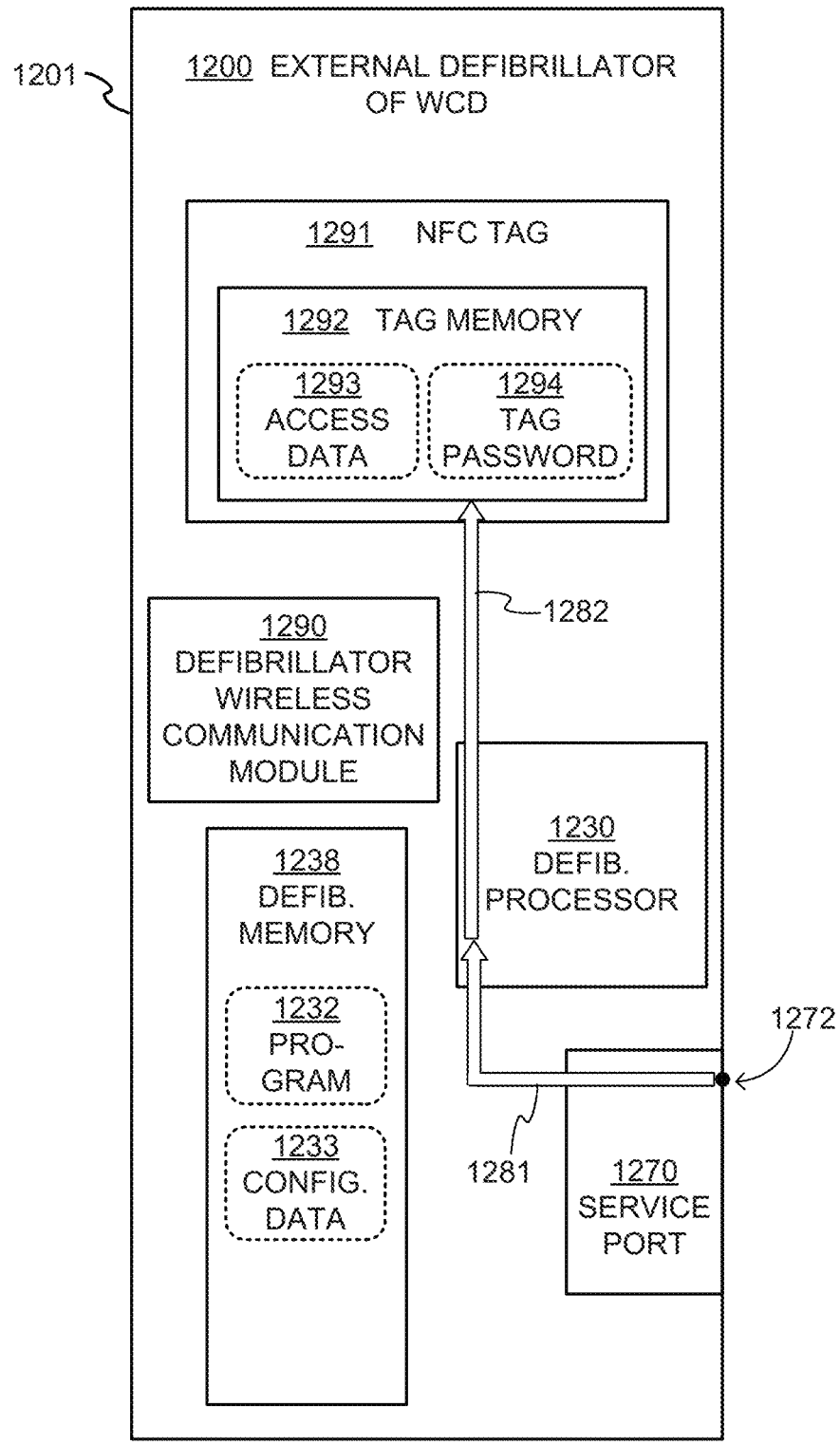
FIG. 12 is a diagram showing sample components of an external defibrillator, such as the external defibrillator of FIG. 3, in an embodiment in which the NFC tag may receive and store updated data via a wired service port.

FIG. 12 is a diagram of sample components of an external defibrillator 1200, such as the one of FIG. 2 and made according to embodiments. External defibrillator 1200 includes a defibrillator housing 1201, which contains therein components as shown for this example. Defibrillator 1200 thus includes a defibrillator processor 1230, a defibrillator memory 1238, a defibrillator wireless communication module (DWCM) 1290 and an NFC tag 1291, all of which could be made as described earlier for similar components of FIG. 3. Similarly, NFC tag 1291 may have a tag memory 1292, which stores access data 1293, and optionally also a tag password 1294. Access data 1293 may be needed for accessing DWCM 1290. Moreover, defibrillator memory 1238 can be configured to store at least one program 1232 and configuration data 1233.

External defibrillator 1200 further includes a service port 1270 in defibrillator housing 1201. Service port 1270 has a contact node 1272 that is electrically coupled with defibrillator processor 1230. For example, service port 1270 can be a port for a USB plug, a port for a serial or parallel cable, and so on. Contact node 1272 may be one of the metal contacts of such a port.

In such embodiments, updated tag data may be received via contact node 1272. This updated tag data may include access data and/or a tag password, which can be stored in tag memory 1292 in lieu of the existing access data and/or a tag password. More particularly, defibrillator processor 1230 can be further configured to store in tag memory 1292 the updated tag data received via contact node 1272. In some embodiments, the path of the updated tag data for this updating operation can be shown in FIG. 12 by two arrows 1281, 1282. This would prevent malicious users from reconfiguring the NFC tag wirelessly in an attempt to use the device for their own purposes.

In some embodiments, the data stored in tag memory 1392 is allowed to be changed only via the wired connection through service port 1272, and for example not wirelessly as in FIG. 10.

In some embodiments it may be desirable for an external defibrillator to stop using a key (symmetric or asymmetric). In this case, the device would be able to update its NFC tag with data encrypted using new keys. New keys may be received from a trusted source either wirelessly, wired, or as stored as backups on the device as seen in the next example.

In some embodiments, the NFC tag may be programmed by data that is backed-up in the defibrillator memory. This can be either for original programming, or in case the tag memory becomes corrupted. An example is now described.

Figure 13:
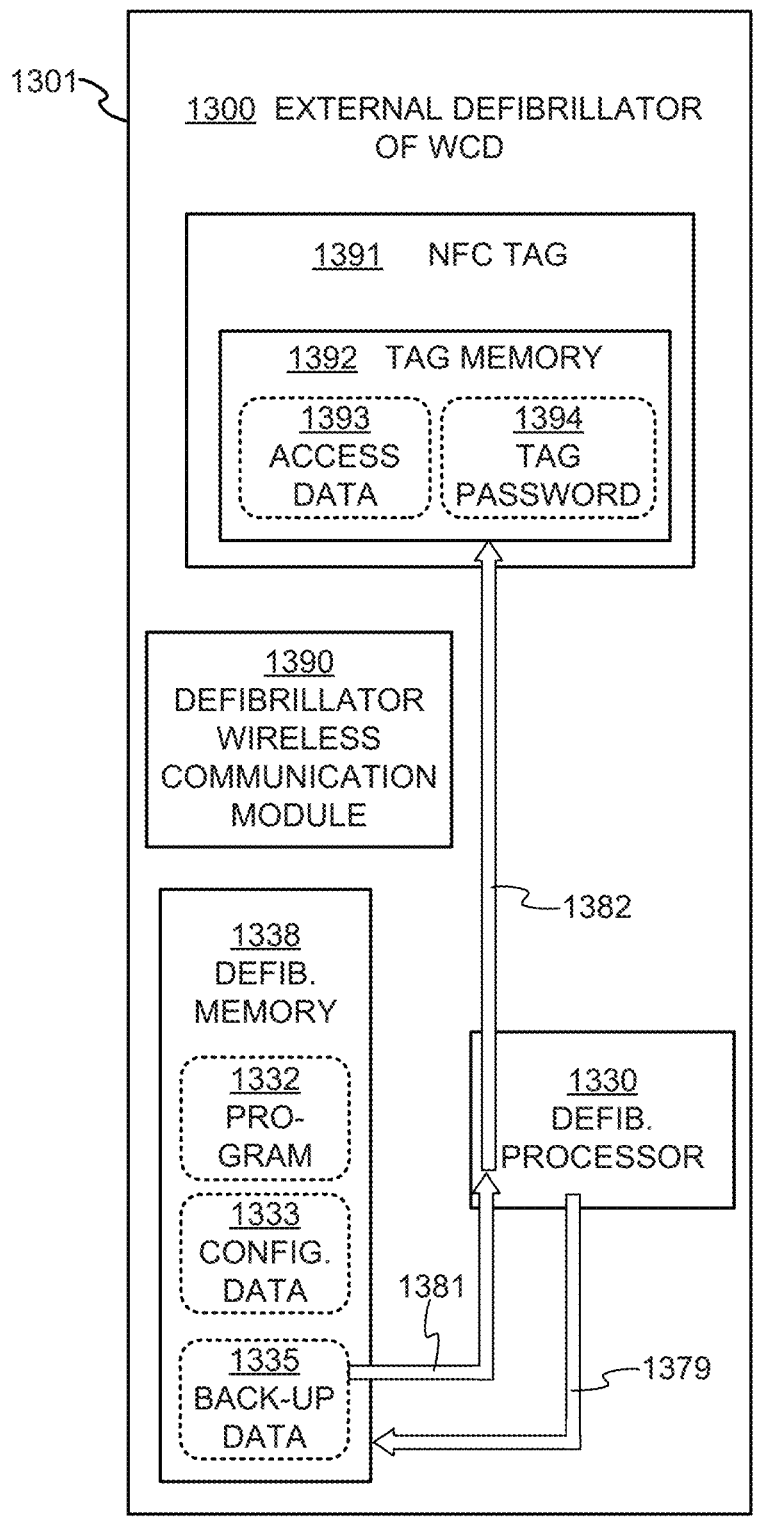
FIG. 13 is a diagram showing sample components of an external defibrillator, such as the external defibrillator of FIG. 3, in an embodiment in which the NFC tag may receive backup data stored in a memory of the external defibrillator.

FIG. 13 is a diagram of sample components of an external defibrillator 1300, such as the one of FIG. 2 and made according to embodiments. External defibrillator 1300 includes a defibrillator housing 1301, which contains therein components as shown for this example. Defibrillator 1300 thus includes a defibrillator processor 1330, a defibrillator memory 1338, a defibrillator wireless communication module (DWCM) 1390 and an NFC tag 1391, all of which could be made as described earlier for similar components of FIG. 3. Similarly, NFC tag 1391 may have a tag memory 1392 that stores access data 1393, and optionally also a tag password 1394. Access data 1393 may be needed for accessing DWCM 1390. Moreover, defibrillator memory 1338 can be configured to store at least one program 1332, configuration data 1333 and back-up data 1335 for backing up NFC tag 1391.

In such embodiments, defibrillator processor 1330 can be further configured to store in tag memory 1392 back-up data 1335 that is stored in defibrillator memory 1338. In some embodiments, the path of the updated tag data for this updating operation can be shown in FIG. 13 by two arrows 1381, 1382. This back-up data 1335 may include access data and/or a tag password, which can be stored in tag memory 1392 in lieu of the existing access data and/or a tag password.

For such embodiments, back-up data 1335 may have become stored in defibrillator memory 1338 in a number of ways. In many of these embodiments, back-up data 1335 is thus previously stored in defibrillator memory 1338 by defibrillator processor 1330, via arrow 1379 that uses an internal connection. And for these embodiments, defibrillator processor 1330 may have received back-up data 1335 in a number of ways.

For a first example, DWCM 1390 may have been further configured to receive wirelessly the back-up data, as shown in FIG. 11, and from there defibrillator processor 1330 may be receiving back-up data 1335 according to a path similar to what is shown by arrow 1181. From there, back-up data 1335 would be stored in defibrillator memory 1338 via arrow 1379.

For a second example, external defibrillator 1300 may have, in its housing 1301, a service port (not shown), similar to service port 1270 of FIG. 12, with a contact node contact node similar to contact node 1272. In this second example, defibrillator processor 1330 can be further configured to receive back-up data 1335 via the contact node according to a path similar to what is shown by arrow 1182. From there, back-up data 1335 would be stored in defibrillator memory 1338 via arrow 1379.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description. Plus, any reference to any prior art in this description is not, and should not be taken as, an acknowledgement or any form of suggestion that such prior art forms parts of the common general knowledge in any country or any art.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

This disclosure, which may be referenced elsewhere as "3330.2", is meant to be illustrative and not limiting on the scope of the following claims. The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

The claimed invention can be better understood in view of the embodiments described and illustrated in the present disclosure. The attentive reader will note, however, that some aspects of the disclosed embodiments may extend beyond the scope of the claims of this document. To the extent that these aspects indeed extend beyond the scope of the claims of this document, then these aspects are to be considered as supplementary background information for better comprehension, and do not constitute definitions of the invention per se for purposes of this document only. Such aspects may, however, constitute definitions of the invention per se for purposes of another, related document.

What is claimed is:

1. A method to authenticate a user of an accessing device of a wearable cardioverter defibrillator (WCD) comprising a support structure configured to be worn by a patient, a power source, an energy storage module configured to be charged from the power source to store an electrical charge, a discharge circuit coupled to the energy storage module, the discharge circuit controllable to discharge the electrical charge through the patient while the support structure is worn by the patient, a defibrillator memory configured to store a program, and a defibrillator processor configured to run the stored program to generate a shock decision, to store in the defibrillator memory action data relating to at least one of the shock decision and inputs for running the program, and to control the discharge circuit to discharge the electrical charge responsive to the shock decision being a decision to shock, the method comprising:
    reading data encoded on the WCD using the accessing device, wherein the encoded data includes access data for the WCD;
    sending the access data to a secure web site to determine if the user of the accessing device has permission to communicate with the WCD;
    receiving permission information from the secure website in response to sending the access data;
    operating with the WCD using the accessing device when the received permission information indicates that the user of the accessing device has permission to operate with the WCD, wherein operating with the WCD includes providing configuration data to the defibrillator memory; and
    delivering the electrical charge as therapy to the patient based on the configuration data stored in the defibrillator memory responsive to the decision to shock.

2. The method of claim 1, wherein the user of the accessing device is unable to operate with the WCD when the received permission information indicates that the user of the accessing device does not have permission to operate with the WCD.

3. The method of claim 1, further comprising communicating updated configuration data to the WCD when the received permission information indicates that the user of the accessing device has permission to operate with the WCD.

4. The method of claim 1, wherein the access data includes a serial number for the WCD, and the serial number is used by the secure website to determine if the user of the accessing device has permission to operate with the WCD.

5. The method of claim 1, further comprising:
    decoding the encoded data read with the accessing device prior to sending the access data to the secure website.

6. The method of claim 1, wherein the permission information includes a security key, and further comprising communicating with the WCD via a secure communication link using the security key.

7. The method of claim 1, further comprising receiving a prompt to exchange validation data with the secure website before receiving the permission information.

8. The method of claim 1, wherein the user of the accessing device is a clinician.

9. The method of claim 1, wherein the configuration data comprises a configuration setting for the WCD specific to the patient.

\* \* \* \* \*